United States Patent
Adden et al.

(10) Patent No.: US 10,786,657 B2
(45) Date of Patent: Sep. 29, 2020

(54) STRUCTURED DRUG-ELUTING BALLOON CATHETER

(75) Inventors: Nina Adden, Nuremberg (DE); Bettina Surber, Gachnang (CH)

(73) Assignee: BIOTRONIK VI Patent AG, Baar (CH)

( * ) Notice: Subject to any disclaimer, the term of this patent is extended or adjusted under 35 U.S.C. 154(b) by 660 days.

(21) Appl. No.: 12/774,894

(22) Filed: May 6, 2010

(65) Prior Publication Data

US 2010/0312182 A1 Dec. 9, 2010

Related U.S. Application Data

(60) Provisional application No. 61/183,991, filed on Jun. 4, 2009.

(51) Int. Cl.
A61M 25/10 (2013.01)

(52) U.S. Cl.
CPC .......... *A61M 25/10* (2013.01); *A61M 25/104* (2013.01); *A61M 25/1029* (2013.01); *A61M 2025/105* (2013.01); *A61M 2025/1031* (2013.01); *A61M 2025/1086* (2013.01); *A61M 2025/1088* (2013.01)

(58) Field of Classification Search
CPC .................. A61M 25/10; A61M 2025/105
USPC ............ 604/103.01–103.02, 103.06, 103.08; 623/1.11; 427/2.1; 424/424
See application file for complete search history.

(56) References Cited

U.S. PATENT DOCUMENTS

| | | | |
|---|---|---|---|
| 4,222,384 A | 9/1980 | Birtwell | |
| 5,824,041 A | 10/1998 | Lenker et al. | |
| 6,893,431 B2 * | 5/2005 | Naimark et al. | 604/891.1 |
| 9,126,025 B2 * | 9/2015 | Ewing | A61M 25/1002 |
| 2004/0044308 A1 * | 3/2004 | Naimark | A61M 25/10 604/103 |
| 2004/0044404 A1 | 3/2004 | Stucke et al. | |
| 2004/0064093 A1 | 4/2004 | Hektner et al. | |
| 2005/0201974 A1 * | 9/2005 | Schestopol | A61K 9/0065 424/78.27 |
| 2006/0212106 A1 | 9/2006 | Weber et al. | |
| 2008/0140002 A1 * | 6/2008 | Ramzipoor et al. | 604/103.02 |

(Continued)

FOREIGN PATENT DOCUMENTS

| | | |
|---|---|---|
| DE | 102 15 462 | 10/2003 |
| EP | 1 604 704 | 12/2005 |

(Continued)

OTHER PUBLICATIONS

European Patent Office, Search Report for Corresponding EPO Application No. 10157039.8, Issued Sep. 28, 2010.

(Continued)

*Primary Examiner* — Nathan R Price
*Assistant Examiner* — Melissa A Snyder
(74) *Attorney, Agent, or Firm* — Greer, Burns & Crain, Ltd.; Steven P. Fallon

(57) ABSTRACT

The invention relates to a balloon catheter featuring—at least on portions of the outward-turned surface of the dilatable area—hair-like extensions, with the average diameter D, the average length L, and the average center-to-center distance P of the hair-like extensions to each other being selected such that a drug on the balloon surface covered with hair-like extensions can essentially be secured by means of capillary forces.

20 Claims, 1 Drawing Sheet

(56) References Cited

U.S. PATENT DOCUMENTS

2008/0169059 A1* 7/2008 Messersmith et al. ....... 156/249
2009/0112239 A1* 4/2009 To .................... A61M 25/1027
                                                           606/159
2010/0312182 A1    12/2010 Adden et al.

FOREIGN PATENT DOCUMENTS

WO       WO 9423787 A1 * 10/1994   ........ A61M 25/1002
WO       WO 02/43796 A2    6/2002
WO    WO 2008/091386       7/2008

OTHER PUBLICATIONS

Geim Ak, Dubonos Sv, Grigorieva Iv, Novoselov Ks, Zhukov Aa, and Shapoval Syu. "Microfabricated adhesive mimicking gecko foot-hair." Nature Materials, vol. 2, Jul. 2003, pp. 461-463.
Office Action issued by the USPTO in U.S. Appl. No. 12/774,931, dated Feb. 4, 2013.
Office Action issued by the USPTO in U.S. Appl. No. 12/774,931, dated Aug. 23, 2012.
Office Action issued by the USPTO in U.S. Appl. No. 12/774,931, dated Apr. 19, 2012.
Amendment A, filed Jul. 17, 2012 in U.S. Appl. No. 12/774,931.
Amendment B, filed Dec. 19, 2012 in U.S. Appl. No. 12/774,931.

\* cited by examiner

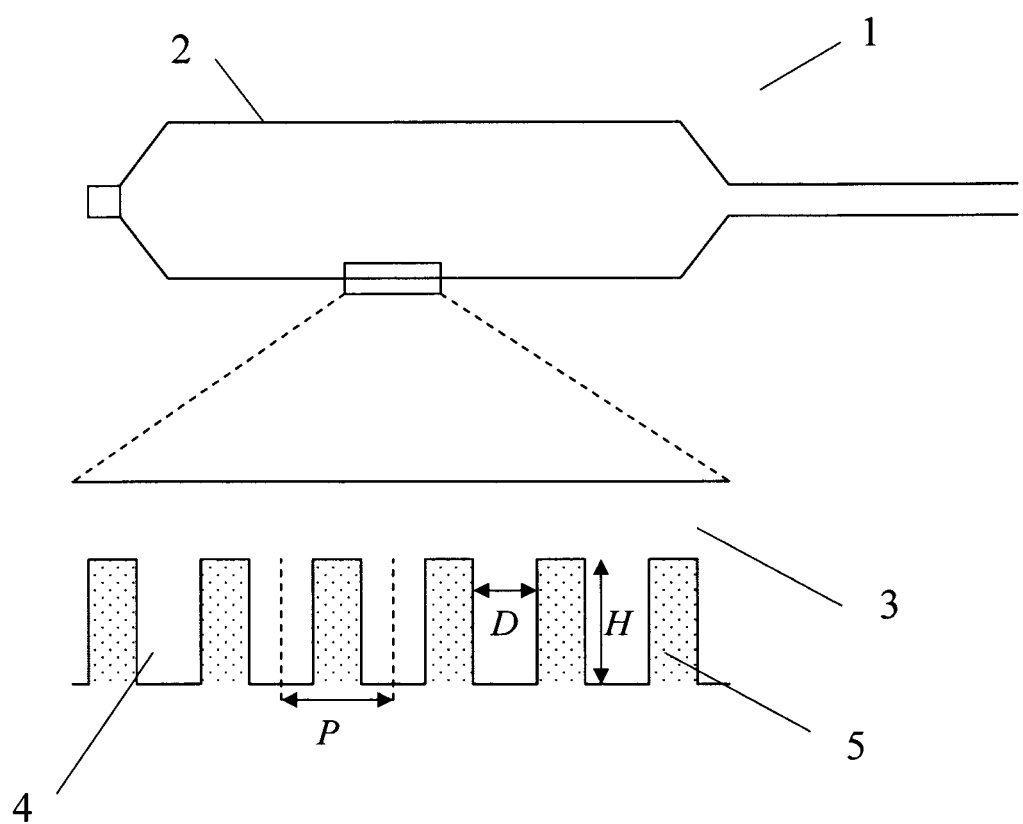

STRUCTURED DRUG-ELUTING BALLOON CATHETER

CROSS REFERENCE

The present application claims priority to U.S. Provisional Application No. 61/183,991 filed on Jun. 4, 2009.

FIELD OF THE INVENTION

The present invention relates to the field of a drug-eluting balloon catheter, as well as to the methods of manufacturing such balloon catheter.

BACKGROUND

Angioplasty, also referred to as percutaneous transluminal angioplasty (PTA) or percutaneous transluminal coronary angioplasty, is a method to dilate or reopen narrowed or blocked blood vessels (mostly arteries, in rarer cases also veins). Balloon dilation is a common angioplasty method.

In interventional radiology, cardiology and angiology balloon dilation within the scope of angioplasty means a method to dilate abnormally narrowed blood vessels using a balloon catheter, an angiocatheter with a balloon attached to it that does only deploy at the narrowed location slowly under high pressure (6-20 bar). This way, the stenoses caused above all by atherosclerotic changes (atherosclerosis) are expanded such that they no longer or less severely obstruct the blood stream.

In this process the balloon catheters are almost always inserted from the groin via a guide wire and a guide catheter into the stenosis and inflated with pressure. Most of the time this eliminates the stenosis and an operation is avoided.

Modern methods in the area of plastics processing allow the design and further development of such balloons to adjust the quality individually to the needs of patients. In this connection, the balloons' flexibility and their resistance to pressure are important.

The drug-eluting balloon catheter or drug-coated balloon catheter represents a further development of conventional balloon catheters.

The balloon surface is coated with a drug or medication that is applied at the site of the stenosis through the balloon's dilation in order to support the dilated vessel pharmacologically and to stabilize it. Compared to stent therapy no mechanically acting foreign object remains inside the body after the intervention.

A cytostatic agent, such as for example Paclitaxel, is frequently used as a drug in this connection, since it rapidly penetrates the vascular wall. Moreover, an additive that expedites the absorption of the drug into the vascular wall is frequently added to the drug.

Various methods are known to apply drugs or medication onto a balloon catheter:
1) Embedding the drug into a microporous surface of the balloon;
2) Coating the balloon with drug-containing polymer coatings (base coating, drug depot).

In conventional methods the majority of the drug is applied under the folds of the non-dilated balloon. The result is an uneven distribution of the drug over a dilated balloon surface, and subsequently, also over the surface of the dilated vessel.

The drug is frequently applied to the balloon through dipping or spraying. During the subsequent dilation the portion of the drug that remained on the outside can uncontrollably flake off, making it impossible to control the release of the inserted drug with precision.

It is also known that drug-eluting balloons release up to 80% of their drug-load into the blood stream, and thus increase the systemic concentration of the drug in an undesired way. Especially with balloons used in large peripheral blood vessels drug concentrations can be reached in the blood that can be compared to chemotherapeutic treatment.

The task of the present invention is to reduce or avoid one or several disadvantages of prior art.

SUMMARY

The task is solved by providing a balloon catheter featuring—at least on portions of the outward-turned surface of the dilatable area—hair-like extensions, with the average diameter D, the average length L, and the average center-to-center distance P of the hair-like extensions to each other being selected such that a drug on the balloon surface covered with hair-like extensions can essentially be secured by means of capillary forces.

Based on the surface structure of the inner surface of gecko feet, one surface of the dilatable balloon features a multitude of hair-like extensions. Since geckos have a multitude of small hairs on their feet in the sub-micrometer range, they can also climb smooth surfaces vertically or even overhead. This effect is a combination of capillary forces and van der Waals forces. In particular, the balloon catheter according to the invention uses the capillary forces of such a surface structure to secure a drug on the balloon surface and, if the need arises, to release it again. This surface structure allows for the balloon to be equally loaded with a drug over a defined surface. Through dipping, for example, the balloon catheter absorbs a defined amount of drug as a result of the capillary forces of the surface structure of the balloon catheter according to the invention, and secures said amount of drug on the surface even after a drying step. A costly application process is not necessary and flaking off of the dried drug from the balloon surface is avoided.

Basically any known balloon catheter system can be used for the balloon catheter according to the invention. The invention especially concerns a balloon catheter featuring an inner sheath, with a distal end of an expandable balloon attached to said inner sheath, and with said balloon at least partially resting against the outer surface of the inner sheath in a non-expanded, deflated state. In particular, the invention concerns such catheters intended to carry a drug on the outside of the deflated balloon, said drug being pressed against a vascular wall at the targeted location following insertion into a vessel and dilation of a stenosis through inflation of the balloon with a fluid, and being released at least in part at said location.

In addition to an inner sheath and the balloon, balloon catheters of the intended kind generally feature an outer sheath as well, such outer sheath reaching at least to a proximal end of the balloon and being connected to the latter in a fluid-tight manner. A fluid line is typically provided between the inner and outer sheath of the catheter running in the longitudinal direction of the catheter from its proximal end up to the balloon's interior, such fluid line resulting for example from the outer sheath having an interior diameter greater than the outer diameter of the inner shaft.

In the interior of the inner shaft a hollow space enclosed by the inner sheath, extending in the longitudinal direction of the inner sheath, is provided as lumen. Said lumen serves, for example, to accept a mandrin or a guide wire. In that case, for example, the catheter and the guide wire are designed such that the guide wire can emerge at the distal tip of the catheter, and that it is to be controlled from the proximal end. Using controlling means, for example, the guide wire is moved such that it can also easily be inserted into branching blood vessels. The balloon catheter can then be pushed along the guide wire.

Irrespective of the type of catheter—especially with respect to the design of the controlling means—the distal end of balloon catheters features the already mentioned expandable balloon. During the insertion of the balloon catheter the balloon is compressed and closely rests against the catheter's inner sheath. By inflating the balloon with a fluid the balloon can be expanded. The balloon expands as soon as the balloon is guided up to the intended location. As a result of the balloon's expansion one surface of the balloon rests against a vascular wall. This occurs, for example, for the purpose of dilating stenosis by means of a balloon catheter.

The balloon catheter according to the invention features hair-like extensions at least on portions of the outward-turned surface of the dilatable area. Especially such areas of the balloon or portions thereof that get in contact with one vascular wall following the balloon's inflation may be provided with hair-like extensions. Preferably, at least 20% of the balloon surface feature hair-like extensions, in particular preferably, 30% to 100% of the balloon surface feature hair-like extensions. The hair-like extensions feature a form that is based on the balloon surface and that rises above it. The hair-like extensions can especially feature one or several lateral surfaces and possibly one surface that is turned away from the balloon surface, and that can be brought in contact with one vascular wall when the balloon is inflated. Preferably, for the mast part the hair-like extensions are cylindrical.

Basically, it is possible to manufacture the hair-like extensions from any material that can be connected to a balloon catheter surface and that is sufficiently tolerable for the use within a human blood vessel. Preferably, the hair-like structures consist of materials or material compositions that feature stability and stiffness, so that the hair-like extensions can stick out upright from the balloon surface rather than collapse onto themselves or bend. The hair-like extensions may in particular be manufactured from the same material from which the outer surface of the balloon's catheter is made. Suitable materials (e.g. polymers) are known to the expert.

A surface with hair-like extensions may be manufactured using different methods. For example, through lithographic methods, such as for example electron beam lithography and laser lithography, or through etching, negative forms may be generated. In a subsequent casting process, the positive surface—starting from the negative form—with hair-like extensions is generated (see for example A. K. Geim et al., Nature Mater. 2, 461-463 (2003) and H. Lee, B. P. Lee and P. B. Messersmith, Nature 448, 338-341 (2007)).

The average diameter D of the hair-like extensions, the average length L of the hair-like extensions, as well as the average center-to-center distance P of the hair-like extensions to each represent parameters that influence the magnitude of the achievable capillary forces. D can be determined by determining and adding the diameters of all hair-like extensions for a selected area, and by then dividing the obtained sum by the number of measured hair-like extensions. L can be determined by determining and adding the lengths of all hair-like extensions for a selected area, and by then dividing the obtained sum by the number of measured hair-like extensions. P can be determined by determining the distances of all hair-like extensions to the respective nearest hair-like extension for a selected area, with measures taken from one center of a first hair-like extension to the center of the nearest hair-like extension. The obtained distance values are added and the obtained sum is divided by the number of measured hair-like extensions.

According to the present invention D, L, and P are selected such that a given drug can be secured on the balloon surface covered with hair-like extensions. Also the material properties of the material used to manufacture the hair-like extensions influences the achievable capillary effects, for example the hydropathy of the material surface. The required capillary forces to secure a certain drug or a solution containing such drug according to the invention on the balloon catheter surface are not the same for every drug or for every solution, and thus must be redetermined for each combination consisting of drug and balloon catheter according to the invention. By conducting routine experiments the expert can determine without difficulties a combination consisting of D, L, and P suitable to secure a given drug on the balloon surface covered with hair-like extensions to the extent desired. Test surfaces can be provided for this purpose that feature hair-like extensions with various combinations of D, L, and P. These test surfaces can then be brought in contact with the desired drug or the desired drug solution, for example by dipping or spraying. If necessary, a drying step can follow, during which solvents can possibly be removed. The amount of drug secured on the test surface is then determined.

D can in particular be selected from a range between 0.1 to 5 μm, preferably from 0.2 to 1 μm. L can in particular be selected from a range of 0.1 to 5 μm, preferably from 0.15 to 2 μm. P can in particular be selected from a range of 0.1 to 7 μm, preferably from 0.5 to 3 μm. Preferably, D and L are selected such that a ratio of D to L results that is selected from a range of 0.5 to 2, preferably 0.75 to 1.5. Preferably, P and D are selected such that a ratio of P to D results that is selected from a range of 1 to 50, preferably from 1.5 to 10.

The balloon catheter according to the invention may feature hair-like extensions, with said hair-like extensions being coated with a polymer having catechol side groups. Suitable polymers as well as polymer composites and methods for coating have been disclosed in WO 08/091386. Such polymers may feature catecholamines such as Dopamine or the amino acid 3,4-dihydroxy-L-Phenylalanine, also known as DOPA. A particularly preferred polymer is poly(Dopamine Methacrylamide (DMA)-co-Methoxyethyl Acrylate (MEA)). Preferred polymers feature catechol side groups, with the catechol side groups featuring at least 5% by weight of the total polymer weight, particularly preferable of 10% by weight to 70% by weight. The coating of the hair-like extensions with a polymer having catechol side groups may feature a coating thickness of less than 100 nm; preferably, the coating thickness is selected from a range between 1 nm and 50 nm.

The present invention also refers to a balloon catheter, in which a drug or a solution containing a drug is secured at least on portions of the surface of the hair-like extensions. In this connection, the balloon catheter may feature a single or several different drugs that may exist as a mixture or separately secured in different areas of the balloon catheter. Preferably, the balloon catheter features at least one drug that is a cytostatic agent, especially Paclitaxel or Docetaxel.

In addition to the drug or the drugs one or several additives can be secured on portions of the surface of the hair-like extensions. As additives substances can be used that are approved as an additive for medicinal products, such as for example antioxidants, softening agents and/or contrast agents. Additives can expedite the absorption of a drug into the cells. Suitable antioxidants are for example ascorbyl palmitate (E304), butylhydroxyanisol (E320), butylhydroxytoluol (E321), gallate, propyl gallate (E310), octyl gallate (E311), dodecyl gallate (lauryl gallate, E312), lecithine (E322), tocopherol (Vitamin E, E306), α-tocopherol (E307), γ-tocopherol (E308), δ-tocopherol (E309), tocotrienol (Vitamin E, E306). Suitable contrast agents include iopamidol (Isovue 370), iohexanol (Omnipaque 350), ioxilan (Oxilan), iopromide, iodixanol (Visipaque 320).

The present invention also refers to a method to manufacture a drug-eluting balloon catheter, with the surface of a balloon catheter according to the invention being brought in contact at least in part with a solution containing a drug or a drug mixture, at least in the area in which the balloon catheter features hair-like extensions, and, if need be, said surface being subsequently subjected to a drying step. Preferably, the drug or the drug solution is brought in contact with the hair-like extensions of the balloon catheter through dipping, steam treatment, spraying or coating. Suitable methods are known to the expert. The capillary forces generated by the arrangement of the hair-like extensions according to the invention ensure that the drug or the drug solution is secured on the balloon catheter's surface. The invention also refers to a balloon catheter that can be manufactured with a method according to the invention.

The invention also includes balloon catheters according to the invention for use in angioplasty, in particular in percutaneous transluminal angioplasty, or percutaneous transluminal coronary angioplasty.

BRIEF DESCRIPTION OF THE DRAWING

FIG. 1 shows an example of an embodiment of a balloon catheter according to the invention.

DETAILED DESCRIPTION

The invention is explained in detail below based on an exemplary embodiment.

The balloon catheter 1 shown in FIG. 1 represents an exemplary embodiment of the balloon catheter according to the invention. The balloon catheter 1 features a dilatable area 2. A majority of hair-like extensions 4 having a certain average diameter D, a certain average length L, and a certain average center-to-center distance P can be found on at least a portion of the outward-turned surface 3 of the dilatable area 2. D, L and P are selected such that capillary forces between the individual hair-like extensions 4 secure a drug solution 5 at least on portions of the surface of the hair-like extensions 4.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

REFERENCE SIGN LIST

1 Balloon catheter
2 dilatable area
3 Portion of the outward-turned surface of the dilatable area 2
4 hair-like extension
5 drug solution

What is claimed is:

1. A balloon catheter featuring at least on portions of an outward-turned surface of a dilatable area thereof hair-like extensions, with an average diameter D, an average length L, and an average center- to-center distance P of the hair-like extensions to each other being selected such that a defined amount of a given drug on the balloon surface covered with hair-like extensions is secured through capillary forces to surfaces of the hair like extensions, and wherein P is at least twice as large as D.

2. The balloon catheter according to claim 1, characterized in that the hair-like extensions are essentially cylindrical, and wherein L is between about 0.1 and 0.9 μm.

3. The balloon catheter according to claim 1, characterized in that D is between about 0.1 to about 5 μm.

4. The balloon catheter according to claim 1, characterized in that L is between about 0.1 to about 5 μm.

5. The balloon catheter according to claim 1, characterized in that P is between about 0.1 to about 7 μm.

6. The balloon catheter according to claim 1, characterized in that a ratio of D to L is between about 0.5 to about 2.

7. The balloon catheter according to claim 1, characterized in that -a ratio of P to D is between about 2 to about 50.

8. The balloon catheter according to claim 1, characterized in that the hair-like extensions are coated with a polymer having catechol side groups.

9. The balloon catheter according to claim 8, characterized in that the coating has a thickness of less than 100 nm.

10. The balloon catheter according to claim 1, characterized in that a drug or a solution containing a drug is secured at least on portions of the surface of the hair-like extensions.

11. The balloon catheter according to claim 10, characterized in that the drug represents a cytostatic agent.

12. A method for manufacturing a balloon catheter of claim 1, characterized in that at least a portion of the outward-turned surface is brought in contact, at least in part, with a solution containing a drug or a drug mixture in the area in which the balloon catheter features hair-like extensions.

13. A balloon catheter for use in angioplasty, in percutaneous transluminal angioplasty, or percutaneous transluminal coronary angioplasty, comprising:
a dilatable area having an outward turned surface,
a plurality of cylindrical extensions on the outward turned surface having an average diameter D between about 0.1 to 5 μm, an average length L between about 0.1 to about 5 μm, and an average center-to-center distance P between about 0.1 to about 7 μm, the D and L dimensions selected to result in a D to L ratio of between about 0.5 to about 2 and a P to D ratio of between about 1.5 to about 50, each of the extensions having a substantially flat top end that is distal from the outward turned surface;
a coating having a thickness of less than about 100 nm on the extensions and comprising a polymer having catechol side groups; and, a defined amount of a given cytostatic agent drug secured to at least a portion of surfaces of the extensions through capillary forces, wherein the defined amount is set by selection of values of D, L, and P.

14. The balloon catheter according to claim 1 wherein L is between about 0.15 and about 2 μm, and D is between about 0.2 and about 1 μm.

15. The balloon catheter according to claim 1 wherein P is between about 0.5 and about 3 µm, and wherein each of the hair-like extensions has a flat top end that is distal from the outward-turned surface.

16. The balloon catheter according to claim 1, wherein a ratio of D to L is between about 0.75 and 1.5, and wherein a ratio of P to D is between about 1.5 and 10.

17. The balloon catheter according to claim 8, wherein the coating thickness is between about 1 nm and about 50 nm.

18. The balloon catheter according to claim 10 wherein the drug is one of Paclitaxel or Docetaxel.

19. The method of manufacturing a drug-eluting balloon catheter of claim 12, wherein the step of bringing the surface in contact comprises one or more of dipping, steam treatment, spraying or coating.

20. The balloon catheter according to claim 1, wherein the hair-like extensions consist of materials or material compositions that provide a stability and stiffness such that the hair-like extensions stick out upright from the balloon surface.

* * * * *